United States Patent
Spurchise

(10) Patent No.: US 7,682,371 B2
(45) Date of Patent: Mar. 23, 2010

(54) DEVICE WITH ACTUATABLE FLUID-COLUMN OCCLUDER FOR PREVENTION OF EMBOLIZATION

(75) Inventor: Matthew F. Spurchise, Peabody, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 765 days.

(21) Appl. No.: 11/339,218

(22) Filed: Jan. 25, 2006

(65) Prior Publication Data
US 2007/0173882 A1    Jul. 26, 2007

(51) Int. Cl.
*A61M 29/00* (2006.01)
(52) U.S. Cl. .................. 606/200; 606/194; 600/585
(58) Field of Classification Search .......... 606/192, 606/194, 200; 600/585
See application file for complete search history.

(56) References Cited

U.S. PATENT DOCUMENTS

| | | | |
|---|---|---|---|
| 3,834,394 A | | 9/1974 | Hunter et al. |
| 4,966,585 A | * | 10/1990 | Gangemi ............... 604/131 |
| 5,201,706 A | * | 4/1993 | Noguchi et al. ........ 604/103.12 |
| 5,968,068 A | | 10/1999 | Dehdashtian et al. |
| 6,168,571 B1 | | 1/2001 | Solar et al. |
| 6,446,717 B1 | | 9/2002 | White et al. |
| 6,682,505 B2 | * | 1/2004 | Bates et al. ............... 604/96.01 |
| 6,706,055 B2 | | 3/2004 | Douk et al. |
| 6,802,825 B2 | * | 10/2004 | Ackerman et al. .......... 604/174 |
| 2004/0010282 A1 | | 1/2004 | Kusleika |
| 2004/0267307 A1 | | 12/2004 | Bagaoisan et al. |
| 2005/0033346 A1 | | 2/2005 | Sater |
| 2005/0131446 A1 | | 6/2005 | Coughlin et al. |
| 2005/0137622 A1 | | 6/2005 | Griffin |

FOREIGN PATENT DOCUMENTS

EP     268068 A2 *  5/1988

* cited by examiner

*Primary Examiner*—Todd E Manahan
*Assistant Examiner*—Jonathan A Hollm

(57) ABSTRACT

A flexible elongate device having a distally mounted occluder for collecting particulate debris in a body lumen. The occluder containing a fixed amount of fluid is reversibly expandable by push-pull actuation from a contracted configuration to a deployed configuration wherein the occluder is expanded into sealing engagement with the wall of the body lumen. The occluder has a distal end axially secured to an elongate inner member and a proximal end attached to a distal end of an outer tubular member. The occluder has an impermeable occluder casing for containing the occluder fluid. The elongate inner member is slidable within the outer tubular member such that relative longitudinal movement between the elongate inner member and outer tubular member changes the length of the occluder and thus redistributes the occluder fluid within the occluder casing to transform the occluder between its contracted and deployed configurations.

6 Claims, 3 Drawing Sheets

DEVICE WITH ACTUATABLE FLUID-COLUMN OCCLUDER FOR PREVENTION OF EMBOLIZATION

FIELD OF THE INVENTION

The invention relates generally to intraluminal devices for containing particulate in the vessels of a patient. More particularly, the invention relates to a catheter having a mechanically actuated fluid-column occluder for containing emboli in a blood vessel during an interventional vascular procedure. Furthermore, the invention concerns a mechanically actuated fluid-column occluder mounted on a guidewire that can also be used to direct an interventional catheter to a treatment site within a patient.

BACKGROUND OF THE INVENTION

Catheters have long been used for the treatment of diseases of the cardiovascular system, such as treatment or removal of stenosis. For example, in a percutaneous transluminal coronary angioplasty (PTCA) procedure, a catheter is used to insert a balloon into a patient's cardiovascular system, position the balloon at a narrowed treatment location, inflate the balloon to expand the narrowing, and remove the balloon from the patient. Another example is the placement of a prosthetic stent in the body on a permanent or semi-permanent basis to support weakened or diseased vascular walls to avoid closure or rupture thereof.

These non-surgical interventional procedures often avoid the necessity of major surgical operations. However, one common problem associated with these procedures is the potential release into the bloodstream of atherosclerotic or thrombotic debris that can embolize distal vasculature and cause significant health problems to the patient. For example, during deployment of a stent, it is possible for the metal struts of the stent to cut into the stenosis and shear off pieces of plaque which become embolic debris that can travel downstream and lodge somewhere in the patient's vascular system. Further, particles of clot or plaque material can sometimes dislodge from the stenosis during a balloon angioplasty procedure and become released into the bloodstream.

Medical devices have been developed to attempt to deal with the problem created when debris or fragments enter the circulatory system during vessel treatment. Practitioners have approached prevention of escaped emboli through use of occlusion devices, filters, lysing, and aspiration techniques. For example, it is known to remove the embolic material by capturing emboli in a filter positioned distal of the treatment area.

Alternatively, an occlusion device may be deployed distally or proximally of the treatment area to block the flow of contaminated blood, which can then be aspirated along with the embolic debris contained therein. Known occlusion guidewires include an occluder membrane surrounding an expandable mechanical structure that is actuatable by push-pull action of a core wire through an outer tubular member. However, such expandable mechanical structure can be complex to fabricate and can add undesirably to the overall collapsed profile of the occlusion guidewire.

Other known occlusion catheters or guidewires include an inflatable occlusion balloon located adjacent the distal end of a hollow guidewire. Dilute radiopaque contrast agent is forced through an inflation lumen to inflate and deflate the occlusion balloon. However, operating the balloon may take longer than desired due to the viscosity of the inflation medium, the small size of the inflation lumen, and the requirement to attach, detach and operate one or more inflation accessories at the proximal end of the catheter or guidewire. Accordingly, there is a need for a simplified, low-profile embolic protection device.

BRIEF SUMMARY OF THE INVENTION

The present invention is a protection device for collecting/containing embolic debris in a body lumen. The protection device includes an outer tubular member, an elongate inner member longitudinally slidable within the outer tubular member, and a mechanically actuated occluder The occluder has a proximal end fixedly sealed about a distal end of the outer tubular member, a distal end axially secured to the elongate inner member and a fixed amount of fluid contained therein. In an embodiment of the present invention, a sliding seal accommodates relative sliding movement between the inner and outer members and prevents leakage of occluder fluid from the occluder. In another embodiment, the occluder has an annular cross-section defined by the coaxial arrangement of an inner and an outer tubular wall. The annular space between the inner and outer walls is filled with a fixed amount of occluder fluid. The inner tubular wall isolates the core wire from occluder fluid. Upon positioning of the occluder within the body lumen distally or proximally of the treatment site, proximal movement of the elongate inner member relative to the outer tubular member forces the ends of the occluder toward each other, thus redistributing the occluder fluid radially outward to deploy the occluder into sealing apposition with a wall of the body lumen.

In various embodiments of the present invention, the occluder may be comprised of an impervious elastomeric material filled with a biocompatible fluid.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

While the following description generally refers to a distal protection device, it should be understood that the invention is also applicable to a proximal protection device, wherein the occluder may be deployed proximally of a treatment site to block flow upstream of the site. A treatment apparatus, such as a catheter, may be delivered via a through lumen in the proximal protection device to provide therapy at the site. See lumen 509 in FIG. 5. Debris generated during the therapy will not move downstream to embolize because of the temporary stasis in the vessel. Fluid that may be contaminated with debris can be aspirated via the through lumen before the occluder is contracted to allow fluid flow to resume.

Figure 1:
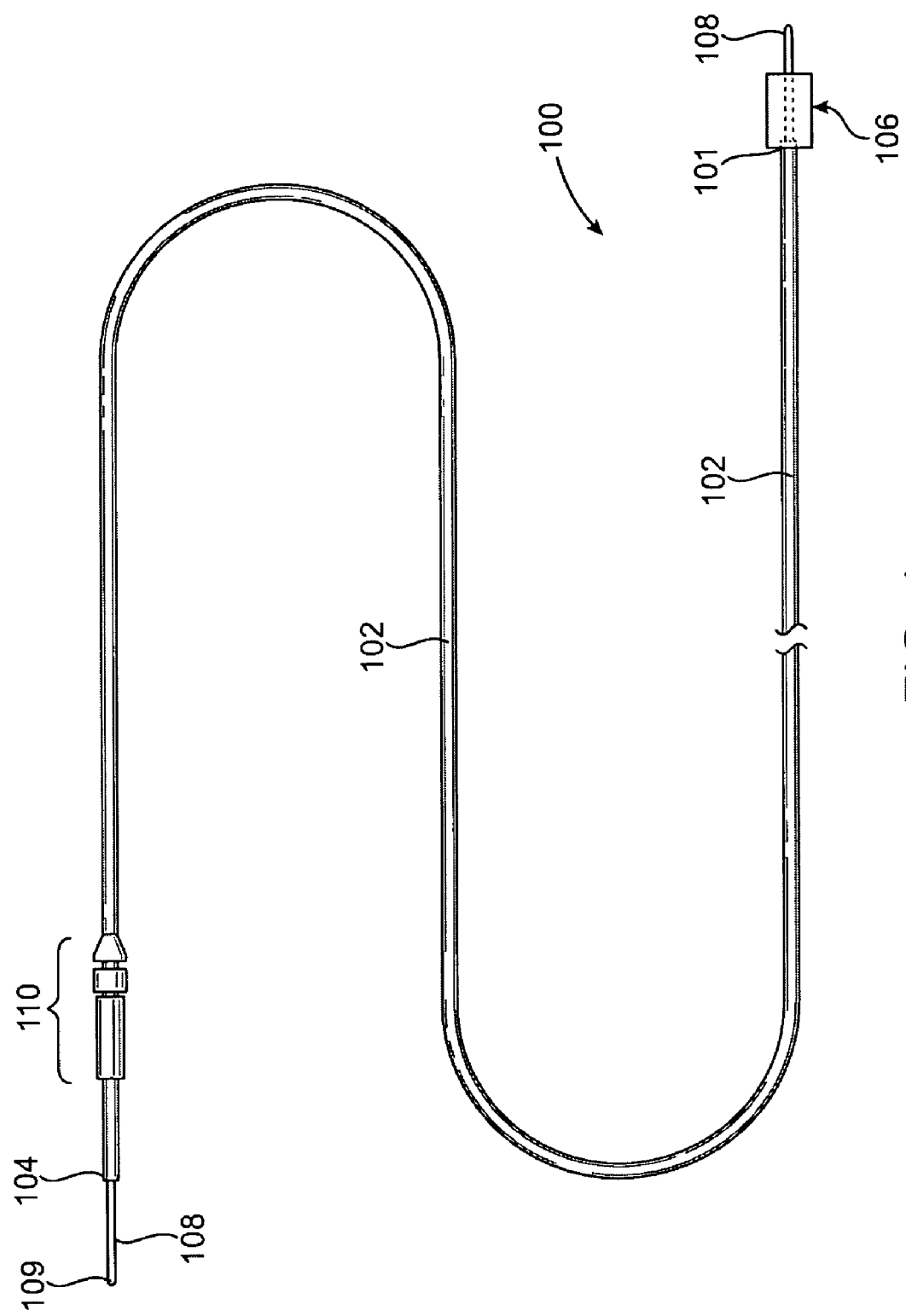
FIG. 1 is a side view of a distal protection device in accordance with an embodiment of the present invention.
Figure 2:
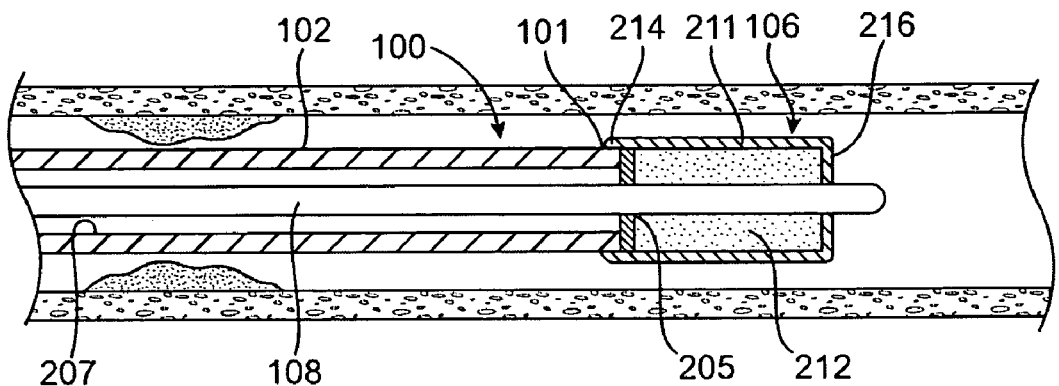
FIG. 2 is a partial cross-section of a distal end of the distal protection device of FIG. 1 within a patient's vascular anatomy.

The present invention is a temporary distal protection device for use in minimally invasive procedures, such as vascular interventions or other procedures, where the practitioner desires to capture and remove embolic material that may be dislodged during the procedure. As shown in FIGS. 1 and 2, distal protection device 100, viz, occluder system 100, includes an elongate tubular member, or catheter shaft, 102, a core wire 108 slidably extending there through, and a hub 110. Core wire 108 extends within a lumen 207 of tubular member 102 from a proximal end 104 to a distal end 101 thereof. A seal 205 is secured to distal end 101 of tubular member 102 and slidingly seals about core wire 108 to retain fluid on the distal, or occluder side of seal 205, like a rod-type seal for a hydraulic cylinder. Alternatively, seal 205 may take the form of a cap that sealingly fits over distal end 101 of tubular member 102. A fluid-column occluder 106 for containing a fixed amount of biocompatible fluid 212 is joined to distal end 101 of tubular member 102 and core wire 108, as described below.

One alternative to rod-type seal 205 is a seal fixed about core wire 108 to slidingly seal anywhere along the interior surface of tubular member 102 to retain fluid on the distal, or occluder side of the seal, like a piston-type seal (not shown) for a hydraulic cylinder. In another alternative embodiment, a rolling diaphragm-type of seal (not shown) can be disposed between tubular member 102 and core wire 108. A seal that allows movement between core wire 108 and shaft 102 may be located at distal end 101, e.g. seal 205, at proximal end 104, or anywhere in lumen 207 between shaft ends 101, 104. If a seal is located at shaft proximal end 104 or within lumen 207 proximally of shaft distal end 101, then the portion of lumen 207 distal to the seal will be in fluid communication with the interior of occluder 106 and thus will also contain occluder fluid 212, which may act as a lubricant between core wire 108 and shaft 102.

Fluid-column occluder 106 has a proximal end 214 and a distal end 216. Occluder distal end 216 is axially secured to core wire 108 and occluder proximal end 214 is attached to distal end 101 of tubular member 102. Occluder ends 214, 216 may be fixedly attached to tubular member 102 and core wire 108, respectively, by use of a bonding sleeve, and/or an adhesive, as would be apparent to one of ordinary skill in the relevant art. Occluder 106 is filled with occluder fluid 212 in the form of gas, liquid, semisolid, i.e. a gel, or combinations thereof. Non-limiting examples of suitable fluids 212 are carbon dioxide gas, saline and silicone oil. Other amorphous, fluid-like substances may be utilized, as long as the substance is biocompatible and is capable of redistributing, deforming or flowing in response to forces applied thereto during push-pull actuation of occluder system 100. In a further embodiment, fluid 212 may comprise suspended radiopaque particles or a dilute or undiluted x-ray contrast agent to aid in fluoroscopic observation of the occluder in vivo. Optionally and/or in addition to fluoroscopic material within fluid 212, radiopaque markers (not shown) may be placed on proximal and distal ends 214, 216 of occluder 106 to aid in fluoroscopic observation during manipulation thereof.

Core wire 108 may be made from a metal, such as nitinol, stainless steel, or cobalt-chromium superalloy wire. In an embodiment of the present invention (not shown), core wire 108 may be tapered at its distal end and/or be comprised of one or more core wire sections of different materials. Core wire 108 may be centerless-ground to have several diameters in its profile in order to provide regions of different stiffnesses with gradual transitions there between. Core wire 108 has a proximal end 109 that extends outside of the patient from proximal end 104 of tubular member 102. Core wire 108 may also include a coiled tip portion, such as, coiled tip portion 326 shown in FIG. 3, or may include a flexible coil spring that is formed from a round or flat coil of stainless steel and/or one of various radiopaque alloys, such as platinum, as is well known to those of skill in the art of medical guidewires.

In another embodiment of the present invention, tubular member or catheter shaft 102 may be constructed of multiple shaft components (not shown) of varying flexibility to provide a gradual transition in flexibility. Such a shaft arrangement is disclosed in U.S. Pat. No. 6,706,055, which is incorporated by reference herein in its entirety. In addition, a liner or axial bearings (not shown) as disclosed in the '055 patent may be utilized between core wire 108 and outer shaft 102 in order to facilitate sliding movement there between during expansion and collapse of occluder 106. In another embodiment, tubular member 102 may be a hollow tube enabling distal protection device 100 to also function as a medical guidewire.

Tubular member 102 may include a thin-walled, tubular structure of a metallic material, such as stainless steel, nitinol, or a cobalt-chromium superalloy. Such metallic tubing is commonly referred to as hypodermic tubing or a hypotube. Metallic tubing formed from other alloys, as disclosed in U.S. Pat. No. 6,168,571, which is incorporated by reference herein in its entirety, may also be used in the tubing of the present invention. In the alternative, outer shaft 102 may include tubing made from a thermoplastic material, such as polyethylene block amide copolymer, polyvinyl chloride, polyethylene, polyethylene terephthalate, polyamide, or a thermoset polymer, such as polyimide.

Figure 4:
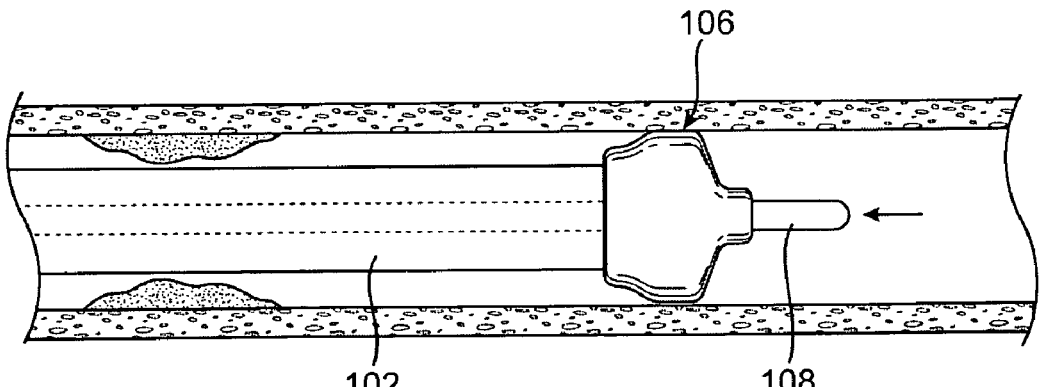
FIG. 4 illustrates a distal end of the distal protection device of FIG. 1 with the occluder in its deployed configuration within the patient's vascular anatomy.

Fluid-column occluder 106 is comprised of an occluder casing 211 that contains occluder fluid 212. Occluder casing 211 is comprised of a biocompatible elastic material that is impermeable to bodily fluids, as well as to the contained occluder fluid 212. In an embodiment of the present invention, occluder casing 211 may be formed from an elastic material such as latex, silicone elastomer, or other viscous forms of natural and synthetic rubbers such as butadiene/acrylonitride copolymers, copolyesters, ethylene vinylacetate (EVA) polymers, ethylene/acrylic copolymers, ethylene/propylene copolymers, polyalkylacrylate polymers, polybutadiene, polybutylene, polyethylene, polyisobutylene, polyisoprene, polyurethane, styrenebutadiene copolymers, and styrene-ethylene/butylene-styrene. Occluder 106 may be made, completely or partially, self-expanding, meaning that occluder 106 may be made to have a mechanical memory to return from the radially contracted or columnar configuration to the radially expanded or deployed configuration, as shown in FIG. 4. Such mechanical memory can be achieved in occluder 106 by making occluder casing 211 in the shape of the deployed configuration, as by casting or blow molding occluder casing 211 inside a hollow mold, or by forming occluder casing 211 over a removable mandrel, e.g. by dipping or thermoforming.

Occluder 106 is sized and shaped such that when it is deployed, as shown in FIG. 4, its greatest diameter will be expanded into sealing contact with the inner surface of the blood vessel wall into which it is placed. The inner surface contact is maintained around the expanded circumference to prevent any emboli from escaping past occluder 106. In the embodiment shown in FIG. 2, occluder casing 211 is of a substantially cylindrical or columnar, radially contracted shape filled with occluder fluid 212, as is occluder casing 511 shown in the embodiment of FIG. 5 that is described further below.

Figure 3:
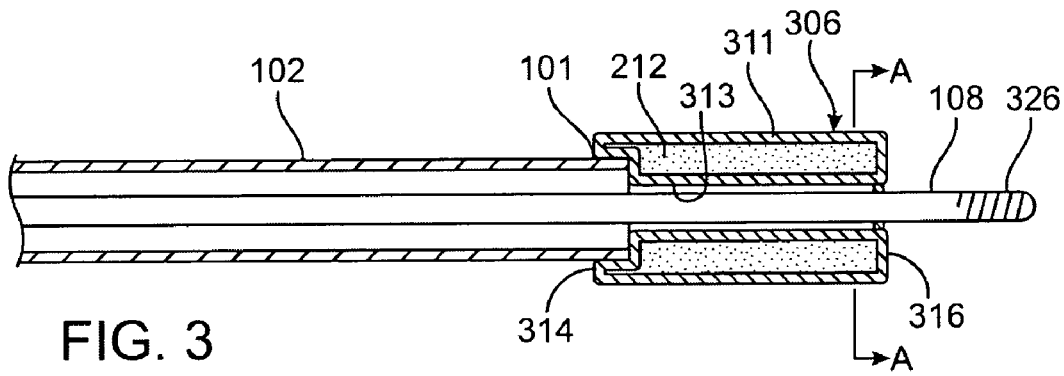
FIG. 3 is a partial cross-section of a distal end of the distal protection device of FIG. 1 in accordance with another embodiment of the present invention.
Figure 3A:
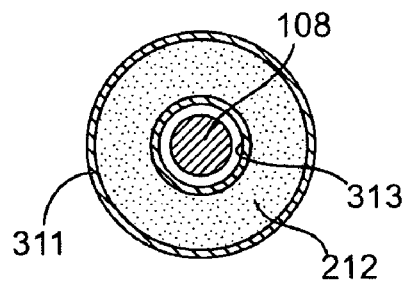
FIG. 3A is a transverse cross-section of the distal protection device of FIG. 3 taken along line A-A.
Figure 3B:
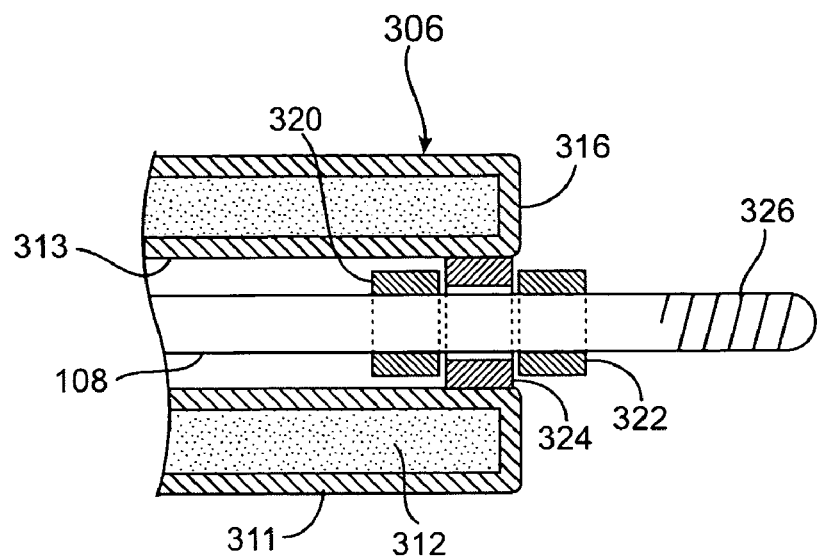
FIG. 3B is an enlarged view of a distal end of the distal protection device of FIG. 3 in accordance with another embodiment of the present invention.

Alternatively, as shown in the embodiment of FIGS. 3, 3A and 3B, occluder casing 311 of occluder 306 has an annular cross-section defined by the coaxial arrangement of an inner tubular wall and an outer tubular wall. The annular space between the inner and outer walls is closed at occluder proximal and distal ends 314, 316 and the fixed internal volume thus defined is filled with a fixed amount of occluder fluid 212, as measured by volume or mass. The inner tubular wall defines a central lumen 313 that surrounds core wire 108 and isolates core wire 108 from occluder fluid 212. As in the embodiment of FIG. 2, occluder distal end 316 is axially secured to core wire 108 and occluder proximal end 314 is attached about distal end 101 of tubular member 102. However, because occluder fluid 212 is contained within annular occluder casing 311 and does not make contact with the portion of core wire 108 within lumen 313, no seal or sealing member is needed to seal distal end 101 of tubular member 102.

In a further embodiment as shown in FIG. 3B, occluder distal end 316 may be axially secured to and rotatable with respect to core wire 108. Occluder distal end 316 may be affixed to a cylindrical collar or bearing 324, such that core wire 108 may rotate relative to occluder 306 and tubular member 102. The bearing may be held in its axial position relative to core wire 108 by proximal and distal stops 320, 322, which are fixedly attached to core wire 108.

Distal protection device 100 is transformable between its radially contracted and deployed configurations by relative movement between proximal and distal ends 214, 216 of fluid-column occluder 106. Distal protection device 100 is tracked through a patient's vasculature with occluder 106 in its low profile, contracted form, as shown in FIG. 2. Once occluder 106 is situated distal of the treatment site, occluder 106 is transformed into its deployed configuration by pulling core wire 108 proximally within tubular member 102, or by pushing tubular member 102 distally over core wire 108. This push-pull actuation draws ends 214, 216 toward each other, thus shortening the length of occluder 106 and redistributing occluder fluid 212 radially outward within occluder casing 211 to thereby bring occluder 106 into contact with the walls of the vessel lumen, as shown in FIG. 4.

If occluder fluid 212 is a gas, then the initial fixed amount, i.e. fixed mass, of fluid 212 may be compressed from its initial volume to a somewhat smaller volume and corresponding increased internal pressure resulting from shortening the length of occluder 106 during push-pull actuation. However, with proper selection of elastic material and thickness for occluder casing 211, a gas-filled embodiment of occluder 106 will expand into its deployed configuration in response to push-pull actuation of distal protection device 100. Occluder 106 is contracted for removal from the body lumen by reversing the push-pull deployment actuation, i.e. by distally advancing core wire 108 relative to tubular member 102 or by proximally drawing tubular member 102 over core wire 108. As described above, fluid-filled occluder 106 is transformable between contracted and deployed configurations by mechanical actuation, not by adding fluid to, or removing fluid from, the interior of occluder 106.

Figure 5:
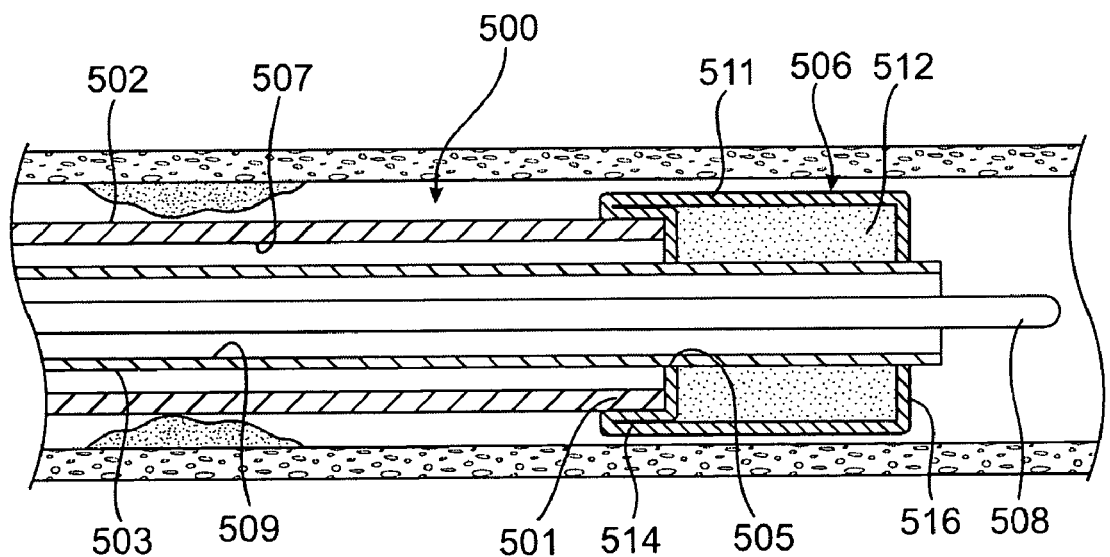
FIG. 5 is a partial cross-section of a distal end of a protection device within a patient's vascular anatomy according to another embodiment of the present invention.

FIG. 5 illustrates a further embodiment of the present invention situated within a body lumen, with an embolic occluder 506 in its contracted configuration. Distal protection device 500 includes occluder 506 attached at a proximal end 514 to a distal end 501 of an outer tubular member or shaft 502 and attached at a distal end 516 to an inner tubular member or shaft 503. Inner tubular member 503 includes a lumen 509 to slidably accommodate a therapy device (not shown) and/or a guidewire 508 therein, whereas outer tubular member 502 includes a lumen 507 to slidably accommodate inner tubular member 503 therein. Occluder ends 514, 516 may be joined to outer and inner tubular members 502, 503, respectively by a bonding sleeve, and/or an adhesive, as would be apparent to one of ordinary skilled in the relevant art. Occluder casing 511 of occluder 506 may be formed from the same elastic materials described above with respect to occluder casing 211, such that occluder proximal end 514 forms integral seal 505 for accommodating sliding movement of inner tubular member 503 there through without leakage of fluid 512 from occluder 506. Alternatively, distal protection device 500 may include a seal positioned and secured between inner and outer tubular members 503, 502, as described above with reference to seal 205 in the embodiment of FIG. 2.

Distal protection device 500 is transformable between its deployed and contracted configurations by relative movement between proximal and distal ends 514, 516 of occluder 506. Distal protection device 500 is tracked through a patient's vasculature over guidewire 508 with occluder 506 in its contracted or columnar configuration, as shown in FIG. 5. Once occluder 506 is situated distal of the treatment site, occluder 506 is transformed into its deployed configuration by pulling inner tubular member 503 proximally relative to outer tubular member 502. This push-pull actuation draws ends 514, 516 toward each other, thus shortening the length of occluder 506 and redistributing occluder fluid 512 radially outward within occluder casing 511 to thereby bring occluder 506 into contact with the walls of the vessel lumen.

Similarly to the embodiment shown in FIG. 2, occluder 506 is contracted for removal from the body lumen by distally advancing inner shaft 503 relative to outer shaft 502. Inner tubular member 503 and outer tubular member 502 may be of any construction or material previously described with reference to tubular member 102.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A distal protection device for collecting debris in a body lumen, comprising:

a hollow tubular member having proximal and distal ends, the tubular member being of a thin-walled metallic material such that the distal protection device functions as a medical guidewire;

a core wire having a flexible coil spring distal tip, the core wire being slidable within the tubular member;

an occluder having an elastic casing, a proximal end fixedly attached to the distal end of the tubular member, a distal end axially secured about the core wire proximal of the flexible coil spring distal tip such that the flexible coil spring distal tip extends distally of the occluder, and a sealed internal volume containing a fixed amount of fluid, the occluder fluid being one of a liquid, a semi-solid, a gel, and a combination thereof; and a seal through which the core wire is slidable, the seal being secured to the distal end of the tubular member and positioned to prevent leakage of the occluder fluid from the occluder, wherein the occluder is adapted to transform between a contracted configuration and an expanded deployed configuration wherein the occluder is in apposition with a wall of the body lumen by relative movement of the core wire and the tubular member.

2. The distal protection device of claim 1, wherein the fluid is redistributable within the elastic casing to cause transformation of the occluder between the contracted configuration and the deployed configuration.

3. The distal protection device of claim 2, wherein the occluder fluid is redistributable by relative movement of the core wire and the tubular member.

4. The distal protection device of claim 1, wherein the occluder casing is selected from a group consisting of latex, silicone elastomer, viscous forms of natural and synthetic rubbers, butadiene/acrylonitride copolymers, copolyesters, ethylene vinylacetate (EVA) polymers, ethylene/acrylic copolymers, ethylene/propylene copolymers, polyalkylacrylate polymers, polybutadiene, polybutylene, polyethylene, polyisobutylene, polyisoprene, polyurethane, styrenebutadiene copolymers, and styrene-ethylene/butylene-styrene.

5. The distal protection device of claim 1, wherein the occluder includes an annular casing having a central lumen for isolating the occluder fluid from the core wire.

6. The distal protection device of claim 5, wherein the occluder distal end is rotateably attached to the core wire.

* * * * *